US008058013B2

(12) United States Patent (10) Patent No.: US 8,058,013 B2
Karl et al. (45) Date of Patent: Nov. 15, 2011

(54) ASSESSING RISK OF DISEASE PROGRESSION IN RHEUMATOID ARTHRITIS PATIENTS

(75) Inventors: Johann Karl, Peissenberg (DE); Veit Peter Grunert, Munich (DE); Wolfgang Rollinger, Rott (DE); Norbert Wild, Geretsried/Gelting (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/412,840

(22) Filed: Mar. 27, 2009

(65) Prior Publication Data

US 2009/0270272 A1 Oct. 29, 2009

Related U.S. Application Data

(63) Continuation of application No. PCT/EP2007/008313, filed on Sep. 25, 2007.

(30) Foreign Application Priority Data

Sep. 29, 2006 (EP) .................................... 06020645
Oct. 19, 2006 (EP) .................................... 06021887

(51) Int. Cl.
*G01N 33/53* (2006.01)
(52) U.S. Cl. ........................................ 435/7.1; 436/518
(58) Field of Classification Search ........................ None
See application file for complete search history.

(56) References Cited

U.S. PATENT DOCUMENTS

| 5,538,853 | A | 7/1996 | Risteli et al. | |
|---|---|---|---|---|
| 5,888,510 | A * | 3/1999 | Kishimoto et al. | ........ 424/141.1 |
| 6,350,907 | B1 * | 2/2002 | Fray et al. | ..................... 562/623 |
| 6,372,442 | B1 | 4/2002 | Bonde et al. | |
| 2006/0063162 | A1 | 3/2006 | Deng | |
| 2007/0036750 | A1 * | 2/2007 | Chou et al. | ................... 424/85.1 |

FOREIGN PATENT DOCUMENTS

| WO | 98/08946 | A1 | 3/1998 |
|---|---|---|---|
| WO | 98/22503 | A3 | 5/1998 |
| WO | 99/28344 | A3 | 6/1999 |
| WO | 99/35167 | A1 | 7/1999 |
| WO | 01/46222 | A3 | 6/2001 |
| WO | 03/050542 | A3 | 6/2003 |

OTHER PUBLICATIONS

Swaak et al. (J. Scan. Rheumatol. 1988 vol. 469-474).*
Madhok et al. (Annals Rheumatic Disease 1993 vol. 52, p. 232-234.*
Amos et al. (British Medical J. 1977 vol. 1, p. 195-197).*
International Search Report issued Jan. 16, 2008 in PCT Application No. PCT/EP2007/008313.
Al-Dehaimi, A. W. et al., Serum Galactosyl Hydroxylysine as a Biochemical Marker of Bone Resorption, Clinical Chemistry, 1999, pp. 676-681, vol. 45, No. 5.
Aman, S. et al., Prediction of disease progression in early rheumatoid arthritis by ICTP, RF and CRP. A comparative 3-year follow-up study, Rheumatology, 2000, pp. 1009-1013, vol. 39.
Arnett, F.C. et al., The American Rheumatism Association 1987 Revised Criteria for the Classification of Rheumatoid Arthritis, Arthritis and Rheumatism, Mar. 1988. pp. 315-324, vol. 31, No. 3.
Badolato, R. and Oppenheimer, J. J., Role of Cytokines, Acute-Phase Proteins, and Chemokines in the Progression of Rheumatoid Arthritis, Seminars in Arthritis and Rheumatism, Oct. 1996, pp. 526-538, vol. 26. No. 2.
Baum, J., Rheumatoid Arthritis: How to Make the Most of Laboratory Tests in the Work-Up, Consultant, May 1998, pp. 1341-1348.
Billinghurst, R. C. et al., Enhanced Cleavage of Type II Collagen by Collagenases in Osteoarthritic Articular Cartliage, J. Clin. Invest, Apr. 1997, pp. 1534-1545, vol. 99, No. 7.
Boini, S. and Guillemin, F., Radiographic scoring methods as outcome measures in rheumatoid arthritis: properties and advantages, Annuals of the Rheumatic Diseases, 2001, pp. 817-827, vol. 60.
Bonde, M. et al., Immunoassay for Quantifying Type I Collagen Degradation Products in Urine Evaluated, Clin. Chem., 1994, pp. 2022-2025, vol. 40, No. 11.
Breiman, L., et al., Classification and Regression Trees, 1984, Wadsworth International Group, Belmont, California.
Breiman, Leo, Random Forests, Machine Learning, Oct. 2001, pp. 5-32, vol. 45.
Bruce, B. and Fries, J. F., The Stanford Health Assessment Questionnaire: Dimensions and Practical Applications, Health and Quality of Life Outcomes, 6 pages, Jun. 9, 2003, vol. 1, No. 20.
Burmeister, G. and Gallacchi, G., A Selective Method for Determining MRP8 and MRP14 Homocomplexes and Heterocomplexes by Sandwich Elisa for the Discrimination of Active and Non-Active Osteoarthritis from Rheumatoid Arthritis in Sera and Synovial Fluids, Inflammopharmacology, 1995, pp. 221-230, vol. 3.
Coste, J. et al. Prediction of Articular Destruction in Rheumatoid Arthritis: Disease Activity Markers Revisited, The Journal of Rheumatology, 1997, pp. 28-34, vol. 24, No. 1.
Duda, R.O. et al. Pattern Classification, 2nd edition, 2001, John Wiley & Sons, Inc., New York, New York.
Dudoit, S. and Van Der Laan, M.J., Asymptotics of cross-validated risk estimation in estimator selection and performance assessment, Statistical Methodology, 2005, pp. 131-154, vol. 2.

(Continued)

*Primary Examiner* — Jacob Cheu

(57) ABSTRACT

Disclosed is an in vitro method aiding in the further assessment of patients suffering from rheumatoid arthritis. The method especially is used in assessing whether an RA patient is at risk of disease progression. The method is for example practiced by analyzing biochemical markers, comprising measuring in a sample the concentration of at least C-reactive protein (CRP) and interleukin-6 and correlating the concentrations determined to the likelihood of an underlying rapidly progressing form of RA. A patient at high risk of a rapidly progressing disease might be a patient in need for treatment or if already treated in need for a different and more effective treatment. The invention also relates to the use of a marker panel comprising C-reactive protein and interleukin-6 in the assessment of a patient with rheumatoid arthritis and it teaches a protein array device and kit, respectively, for performing the method of the invention.

2 Claims, 5 Drawing Sheets

OTHER PUBLICATIONS

Felson, D. T. et al. American College of Rheumatology Preliminary Definition of Improvement in Rheumatoid Arthritis, Arthritis & Rheumatism, Jun. 1995, pp. 727-735, vol. 38, No. 6.

Foell, D. et al., Expression of the pro-inflammatory protein S100A12 (EN-RAGE) in rheumatoid and psoriatic arthritis, Rheumathology, 2003, pp. 1383-1389, vol. 42.

Friedman, J. H., Regularized Discriminant Analysis, Journal of the American Statistical Association, Mar. 1989, pp. 165-175, vol. 84.

Gearing, A. J. H. et. al., Soluble Forms of Vascular Adhesion Molecules, E-Selectin ICAM-1, and VCAM-1: Pathological Significance, Annals New York Academy of Sciences, 1992, pp. 324-331, vol. 667.

Genant, H. K., Methods of Assessing Radiographic Change in Rheumatoid Arthritis: American Journal of Medicine, Dec. 30, 1983, pp. 35-47, vol. 75.

Gineyts, E. et al., Urinary excretion of glucosyl-galactosyl pyridinoline: a specific biochemical marker of synovium degradation, Rheumatology, 2001, pp. 315-323, vol. 40.

Goronzy, J. J. et al., Prognostic Markers of Radiographic Progression in Early Rheumatoid Arthritis, Arthritis & Rheumatism, Jan. 2004, pp. 43-54, vol. 50, No. 1.

Gundberg, C. M. et al., Biology, Physiology, and Clinical Chemistry of Osteocalcin, Journal of Clinical Ligand Assay, Summer 1998, pp. 128-138, vol. 21, No. 2.

Hasegawa, J., Bone Resorption and Inflammatory Inhibition Efficacy of Intermittent Cyclical Etidronate Therapy in Rheumatoid Arthritis, Journal of Rheumatoloy, 2003, pp. 474-479, vol. 30.

Hastie, T. et al. Springer Series in Statistics, The Elements of Statistical Learning, 2001, Springer-Verlag, New York.

Ishiguro, N. et al., Relationships of Matrix Metalloproteinases and Their inhibitors to Cartilage Proteoglycan and Collagen Turnover and Inflammation as Revealed by Analyses of Synovial Fluids From Patients With Rheumatoid Arthritis, Arthritis & Rheumatism, Nov. 2001, pp. 2503-2511, vol. 44, No. 11, Wiley-Liss, Inc.

Kaufmann, J. et al., Hydroxypyridinium collagen crosslinks in serum, urine, synovial fluid and synovial tissue in patients with rheumatoid arthritis compared with osteoarthritis, Rheumatology, 2003, pp. 314-320, vol. 42.

Knott, L. and Bailey, A. J., Collagen Cross-Links in Mineralizing Tissues: A Review of Their Chemistry, Function, and Clinical Relevance, Bone, Mar. 1998, pp. 181-187, vol. 22, No. 3.

Larsen, A. et al., Radiographic Evaluation of Rheumatoid Arthritis and Related Conditions by Standard Reference Films, Acta Radiologica Diagnosis, Jul. 1977, pp. 481-491, vol. 4.

Lee, D. M. and Schur, P. H., Clinical utility of the anti-CCP assay in patients with rheumatic diseases, Annals of the Rheumatic Diseases, 2003, pp. 870-974, vol. 62.

Lorenzo, P. et al., A Novel Cartilage Protein (CILP) Present in the Mid-zone of Human Articular Cartilage Increases with Age, Journal of Biological Chemistry, Sep. 4, 1998, pp. 23463-23468, vol. 273, No. 36.

McLachlin, G. J., Discriminant Analysis and Statistical Pattern Recognition, 1992, John Wiley & Sons, Inc., New York.

Meyer, O. et al., Serial determination of cyclic citrullinated peptide autoantibodies predicted five-year radiological outcomes in a prospective cohort of patients with early rheumatoid arthritis, Arthritis Research & Therapy, 2006, R40, 8 pages, vol. 8, No. 2.

Mueller-Ladner, U. et al., MIA (melanoma inhibitory activity): a potential serum marker for rheumatoid arthritis, Rheumatology, 1999. pp. 148-154, No. 38.

Pepe, M. S., The Statistical Evaluation of Medical Tests for Classification and Prediction, 2003, Oxford University Press, Inc., New York.

Pietrewicz, E. et al., Cytokine levels in serum of patients with juvenile idiopathic arthritis depending on subtype and disease activity, Immunochemistry, Dec. 14, 2004, pp. 232-234, vol. 17, No. 99, Database CA Online, Accession No. 2004-1067747 [XP-002431662].

Pruijn, G. J. M. et al., Anti-CCP Antibody Detection Facilitates Early Diagnosis and Prognosis of Rheumatoid Arthritis, Current Rheumatology Reviews, 2005, pp. 1-7, vol. 1, No. 1, Bentham Science Publishers Ltd.

Rau, R. and Wassenberg, S., Bildgebende Verfahren in der Rheumatologie: Scoring-Methoden bei der rheumatoiden Arthritis, Z. Rheumatol, 2003, pp. 555-565, vol. 62.

Rooney, T.P. et al., Serum Biomarkers for Disease Activity and Radiographic Progression in Patients Receiving Biologic Therapies for Rheumatoid Arthritis, Arthritis & Rheumatism 52, Suppl. S (2005) S564 & 69th Annual Scientific Meeting of the American-College-of-Rheumatology / 40th Annual Scientific Meeting; San Diego, CA, USA, Nov. 12-17, 2005.

Ruczinski, I. et al., Logic Regression, Journal of Computational and Graphical Statistics, 2003, pp. 475-511, vol. 12, No. 3.

Sawai, T. and Uzuki, M., Dynamics of Hyaluronate in Patients with Rheumatoid Arthritis, Connective Tissue, 2001, pp. 253-259, vol. 33.

Saxne, T. et al., Increased Release of Bone Sialoprotein into Synovial Fluid Reflects Tissue Destruction in Rheumatoid Arthritis, Arthritis & Rheumatism, Jan. 1995, pp. 82-90, vol. 38, No. 1.

Saxne, T. and Heinegard, D., Cartilage Oligomeric Matrix Protein: A Novel Marker of Cartilage Turnover Detectable in Synovial Fluid and Blood, British Journal of Rheumatology, 1992, pp. 583-591, vol. 31.

Schellekens, G.A. et al., The Diagnostic Properties of Rheumatoid Arthritis Antibodies Recognizing a Cyclic Citrullinated Peptide, Arthritis & Rheumatism, Jan. 2000, pp. 155-163, vol. 43, No 1.

Sharp, J.T. et al., Methods of Scoring the Progression of Radiologic Changes in Rheumatoid Arthritis, Arthritis and Rheumatism, 1971, pp. 706-720, vol. 14.

Sharp, J.T. et al., How Many Joints in the Hands and Wrists Should Be Included in a Score of Radiologic Abnormalities Used to Assess Rheumatoid Arthritis?, Arthritis and Rheumatism, Dec. 1985, pp. 1326-1335, vol. 28, No. 12.

Straub, R.H. et al., Decrease of Interleukin 6 during the First 12 Months is a Prognostic Marker for Clinical Outcome during 36 Months Treatment with Disease-Modifying Anti-Rheumatic Drugs, British Journal of Rheumatology, 1997, pp. 1298-1303, vol. 36.

Suzuki, F., Roles of Cartilage Matrix Proteins, Chondromodulin-I and -II, in Endochondral Bone Formation: A Review, Connective Tissue Research, 1996, pp. 303-307, vol. 35(1-4).

Syversen, S.W. et. al., Prediction of 10-Year Radiographic Progression in Patients with Rheumatoid Arthritis (RA): The Combined Contribution of Anti-CCP, Rheumatoid Factor and Acute Phase Reactants, Abstract, Ann Rheum Dis, Jun. 23, 2006, p. 110, vol. 65 (Suppl II).

Talamo, J. et al., Use of the Short Form 36 (SF36) for Health Status Measurement in Rheumatoid Arthritis, British Journal of Rheumatology, 1997, pp. 463-469, vol. 36.

Tijssen, P., Chapter 11, Preparation of enzyme-antibody or other enzyme-macromolecule conjugates, Practice and Theory of Enzyme Immunoassays, 1990, pp. 221-278, Elsevier, Amsterdam-New York.

Vallbracht, I. et al., Diagnostic and clinical value of anti-cyclic citrullinated peptide antibodies compared with rheumatoid factor isotypes in rheumatoid arthritis, Ann Rheum Dis, 2004, pp. 1079-1084, vol. 63.

Van Der Heijde, D. et al., Presentation and Analysis of Data on Radiographic Outcome in Clinical Trials, Arthritis & Rheumatism, Jan. 2005, pp. 49-60, vol. 52, No. 1.

Van Der Heijde, D. M. F. M., Joint Erosions and Patients with Early Rheumatoid Arthritis, British Journal of Rheumatology, 1995, pp. 74-78, vol. 34, Suppl, 2.

Van Der Heijde, D. M. et al., Effects of Hydroxychloroquine and Sulphasalazine on Progression of joint Damage in Rheumatoid Arthritis, The Lancet, May 13, 1989, pp. 1036-1038.

Van Gestel, A. M. et al., Development and Validation of the European league Against Rheumatism Response Criteria for Rheumatoid Arthritis, Arthritis & Rheumatism, Jan. 1996, pp. 34-40, vol. 39, No. 1.

Van Paassen, P. et al, Laboratory assessment in musculoskeletal disorders, Best Practice & Research Clinical Rheumatology, 2003, pp. 475-494, vol. 17, No. 3.

Visser, H. et al., How to Diagnose Rheumatoid Arthritis Early a Prediction Model for Persistent (Erosive) Arthritis, Arthritis & Rheumatism, Feb. 2002, pp. 357-365, vol. 46, No. 2.

Zweig, M. H. and Campbell, G., Receiver-Operating Characteristic (ROC) Plots: A Fundamental Evaluation Tool in Clinical Medicine, Clinical Chemistry, 1993, pp. 561-577, vol. 39, No. 4.

European Search Report issued May 10, 2007 in EP Application No. 06020645.5.

International Preliminary Report on Patentability issued Jan. 20, 2009 in PCT Application No. PCT/EP2007/008313.

* cited by examiner

Cumulative Probability Plot of change from baseline after 1 year, n=240

IL-6

ASSESSING RISK OF DISEASE PROGRESSION IN RHEUMATOID ARTHRITIS PATIENTS

RELATED APPLICATIONS

This application is a continuation of PCT/EP2007/008313 filed Sep. 25, 2007 and claims priority to EP 06020645.5 filed Sep. 29, 2006.

FIELD OF THE INVENTION

The present invention relates to an in vitro method aiding in the further assessment of patients suffering from rheumatoid arthritis. The method especially is used in assessing whether an RA patient is at risk of disease progression. The method is for example practiced by analyzing biochemical markers, comprising measuring in a sample the concentration of at least C-reactive protein (CRP) and interleukin-6 and correlating the concentrations determined to the likelihood of an underlying rapidly progressing form of RA. A patient at high risk of a rapidly progressing disease might be a patient in need for treatment or if already treated in need for a different and more effective treatment. The invention also relates to the use of a marker panel comprising C-reactive protein and interleukin-6 in the assessment of a patient with rheumatoid arthritis and it teaches a protein array device and kit, respectively, for performing the method of the invention.

BACKGROUND OF THE INVENTION

Rheumatoid arthritis ("RA") is a chronic, inflammatory, systemic disease that produces its most prominent manifestations in affected joints, particularly those of the hands and feet. The onset of rheumatoid arthritis can occur slowly, ranging from a few weeks to a few months, or the condition can surface rapidly in an acute manner.

RA has a worldwide distribution and involves all ethnic groups. Although the disease can occur at any age, the prevalence increases with age and the peak incidence is between the fourth and sixth decade. The prevalence estimates for the North American population vary from 0.3% to 1.5%. Today, over 2,500,000 individuals are diagnosed with rheumatoid arthritis in the United States alone, with some statistics indicating from 6.5 to 8 million potentially afflicted with the disease. Women are affected 2-3 times more often than men.

The early symptoms of rheumatoid arthritis are mostly joint specific such as painful joints with joint swelling or tenderness, but may also include rather non-specific manifestations like stiffness, fever, subcutaneous nodules, and fatigue. Very characteristic is the symmetric involvement of joints. The joints of the hands, feet, knees and wrists are most commonly affected, with eventual involvement of the hips, elbows and shoulders. As the disease progresses, any type of motion becomes very painful and difficult leading eventually to a loss of function of the involved joints. The more severe cases of rheumatoid arthritis can lead to intense pain and joint destruction. Some 300,000 bone and joint replacement surgical procedures are performed annually in an effort to alleviate the pain and mobility loss resultant from arthritis related joint destruction.

The most widely used system to classify RA is the American College of Rheumatology 1987 revised criteria for the classification of RA (Arnett, F. C., et al., Arthritis Rheum. 31 (1988) 315-324). According to these criteria (known as ARA-criteria), a patient is said to have RA if the patient satisfies at least four of the following seven criteria, wherein criteria 1-4 must be present for at least six weeks: 1) morning stiffness for at least one hour, 2) arthritis of three or more joint areas, 3) arthritis of hand joints, 4) symmetrical arthritis, 5) rheumatoid nodules, 6) serum rheumatoid factor ("RF"), and 7) radiographic changes. These criteria have a sensitivity and specificity of approximately 90%.

The histological changes in RA are not disease-specific but largely depend on the organ involved. The primary inflammatory joint lesion involves the synovium. The earliest changes are injury to the synovial microvasculature with occlusion of the lumen, swelling of endothelial cells, and gaps between endothelial cells, as documented by electron microscopy. This stage is usually associated with mild proliferation of the superficial lining cell layer. Two cell types constitute the synovial lining: bone marrow derived type A synoviocyte, which has macrophage features, and mesenchymal type B synoviocyte. Both cell types contribute to synovial hyperplasia, suggesting a paracrine interaction between these two cell types. This stage of inflammation is associated with congestion, oedema, and fibrin exudation. Cellular infiltration occurs in early disease and initially consists mainly of T lymphocytes. As a consequence of inflammation, the synovium becomes hypertrophic from the proliferation of blood vessels and synovial fibroblasts and from multiplication and enlargement of the synovial lining layers.

Granulation tissue extends to the cartilage and is known as pannus. The tissue actively invades and destroys the periarticular bone and cartilage at the margin between synovium and bone, known as erosive RA.

The articular manifestations of RA can be placed in two categories: reversible signs and symptoms related to inflammatory synovitis and irreversible structural damage caused by synovitis. This concept is useful not only for staging disease and determining prognosis but also for selecting medical or surgical treatment. Structural damage in the typical patient usually begins sometime between the first and second year of the disease (van der Heijde, D. M., et al., Br. J. Rheumatol. 34, Suppl. 2 (1995) 74-78). Although synovitis tends to follow a fluctuating pattern, structural damage progresses as a linear function of the amount of prior synovitis.

The aetiology of the early events in RA remains elusive. An autoimmune component is widely accepted today but other factors are still disputed. The possibility of a bacterial or viral infection has been vigorously pursued. All efforts to associate an infectious agent with RA by isolation, electron microscopy, or molecular biology have failed. It is possible that there is no single primary cause of RA and that different mechanisms may lead to the initial tissue injury and precipitate synovial inflammation.

Clinical signs of synovitis may be subtle and are often subjective. Warm, swollen, obviously inflamed joints are usually seen only in the most active phases of inflammatory synovitis. Cartilage loss and erosion of periarticular bone are the characteristic features of structural damage. The clinical features related to structural damage are marked by progressive deterioration functionally and anatomically. Structural damage to the joint is irreversible and additive.

Data from longitudinal clinical and epidemiologic studies provide guidelines for treatment. These studies emphasize 1) the need for early diagnosis, 2) identification of prognostic factors, and 3) early aggressive treatment. Earlier diagnosis and treatment, preferably within the first several months after onset of symptoms, may help prevent irreversible joint damage.

The effective treatment of rheumatoid arthritis generally comprises a combination of medication, exercise, rest and proper joint protection therapy. The therapy for a particular patient depends on the severity of the disease and the joints that are involved. Non-steroidal anti-inflammatory drugs, corticosteroids, gold salts, methotrexate and systemic immunosuppressants are widely used to reduce inflammation and joint destruction. The use of steroids and immunosuppressants, however, has significant risks and side effects both in terms of toxicity and vulnerability to potentially lethal conditions. More recently therapeutics based on "biologicals" have been introduced into RA-therapy. Such therapeutics, e.g., are soluble receptors or antibodies directed against TNF-α that significantly reduce inflammation. Though very promising, biologicals are still in limited use due to high costs.

The ideal scenario for establishing a diagnosis or assessing the risk of disease progression would be a situation wherein a single event or process would cause the respective disease as, e.g., in infectious diseases. In all other cases correct diagnosis can be very difficult, especially when the etiology of the disease is not fully understood as is the case for RA. Therefore in RA, generally various clinical symptoms and biological markers are considered together for diagnosis of RA or for assessing the risk of disease progression.

The first biochemical marker and the only one generally accepted (see the above ARA-criteria) for aiding in the diagnosis of RA is the rheumatoid factor (RF) as detected in serum. Recently a novel marker called anti-CCP has been introduced. It has been confirmed in many independent studies that autoantibodies to cyclic citrullinated peptides (anti-CCPs) represent a highly sensitive and specific marker for diagnosis of RA.

Anti-CCPs have been intensively studied during the past years by several groups of researchers (cf., e.g., WO 98/08946; WO 98/22503; WO 99/28344; WO 99/35167; WO 01/46222; and WO 03/050542). Recently Schellekens and co-workers (Schellekens, G. A., Arthritis Rheum. 43 (2000) 155-163) reported that an ELISA-test based on specific cyclic citrullinated peptides (CCP) showed superior performance characteristics with regard to diagnostic accuracy for RA as compared to the same assay using linear peptides.

Auto-antibodies against CCP, i.e., antibodies which most likely are reactive with citrullinated polypeptides circulating in a patient serum and which bind to CCP in an in vitro assay are termed "anti-CCP". The patent application of van Venroji et al. (WO 98/22503) describes certain citrullinated peptides and shows that cyclization leads to an improved reactivity of autoantibodies to the these peptides. By using improved CCPs as an antigen for detection of anti-CCP antibodies the sensitivity is increased to 63% as compared to 36% to the corresponding linear peptides. Since autoantibodies in patient sera have slightly different reactivity to different cyclic peptides a combination of peptides was suggested in WO 98/22503 to further improve the assay.

Many research groups have recently shown and confirmed that anti-CCP is an even more sensitive and specific marker for establishing the diagnosis of RA as compared to RF. Anti-CCP autoantibodies are highly specific for RA (ca. 97% specificity), with a sensitivity comparable to that of RF (65-80%) (Lee, D. M. and Schur, P. H., Ann. Rheum. Dis. 62 (2003) 870-874; Pruijn, G. J. M., et al., Curr. Rheumatol. Rev. 1 (2005) 1-7; Vallbracht, T., et al., Ann. Rheum. Dis. 63 (2004) 1079-1084). Furthermore it is of additional diagnostic value that anti-CCP can be detected in a significant percentage of seronegative RA patients (van Paassen, P., et al., Best Pract. Res. Clin. Rheumatol. 17 (2003) 475-494; Vallbracht, I., et al., Ann. Rheum. Dis. 63 (2004) 1079-1084; Schellekens, G. A., et al., Arthritis and Rheumatism 43 (2000) 155-163). This means that anti-CCP autoantibodies are present in a significant fraction of patients (sero-) negative for RF.

As discussed above, establishing a diagnosis of RA and deciding for the optimal treatment option is not an easy task. The course of disease in individual RA patients varies significantly. No unique and generally accepted set of indicators for poor outcome in RA exists to date. Indicators associated with a bad prognosis include e.g. cumulative joint inflammation, high ESR or CRP levels, RF positivity, early radiological erosions, poorer scores for function and adverse socioeconomic circumstances.

To make things even more complicated, assessing a prognosis in RA also suffers from a lack of a clear and generally accepted definition of disease progression.

Several scores—on the basis of clinical symptoms, radiographic changes or physical function—have been developed in order to assess treatment response in RA. However, most of these scores are used in clinical trials settings only, but rarely or not at all in rheumatology practices. Examples are the different response criteria devised by the American College of Rheumatology (ACR) and the European League against Rheumatism (EULAR) (Felson, D. T., et al., Arthritis and Rheumatism 38 (1995) 727-735; van Gestel, A. M., et al., Arthritis and Rheumatism 39 (1996) 34-40). Both—the ACR improvement criteria and the EULAR response criteria—are widely used in clinical trial settings, but not in clinical practice. The same is true for the scoring systems for assessment of radiographic changes according to Sharp or Larsen and several modifications thereof are available to date. Although X-rays are taken for monitoring of radiographic disease progression at regular intervals, they are only compared to previous X-rays but not scored.

Furthermore, in Europe the DAS (disease activity score) and simplifications thereof (DAS28, SDAI, CDAI) are widely used for disease monitoring under therapy. The DAS includes tender and swollen joint counts, ESR or CRP and a global assessment of disease activity (using a VAS—visual analog scale). To a minor extent also assessments of physical function do play a role in monitoring of disease states. These are based on different patient questionnaires—the most widely used in RA being the HAQ (Health Assessment Questionnaire) (Bruce, B. and Fries, J. F., Health Qual Life Outcomes 1 (2003) 20) and the SF-36 (Short Form 36) (Talamo, J., et al., Brit. J. Rheumatol. 36 (1997) 463-469).

However, the above mentioned tools are far from optimal. They are time-consuming and influenced by subjective assessments, e.g. in case of the HAQ or tender/swollen joint counts.

Recently, attempts have been made to further assess various aspects of RA by including more biochemical markers into such assessment or to even base such assessment on biochemical markers.

Coste, J., et al. (The Journal of Rheumatology 24 (1997) 28-34) have investigated twenty clinical and laboratory parameters for their ability to predict articular destruction in RA. Statistical significant correlations to disease progression were found for iron, CRP, ESR, and α1-acid glycoprotein. However, correlations were not very strong and only existing for the first 6 months of follow-up.

Aman, S., et al., Rheumatology 39 (2000) 1009-1013 investigated whether disease progression in RA could be predicted by the markers ICTP, RF and CRP. They found odds ratios from 2.6 to 3.9 for the individual markers and the best marker ratio had an odds ratio of 9.1. This odds ratio translated to a specificity of 71% at a sensitivity of 77%. However, a specificity of 71% is rather low, because in clinical routine a specificity of at least 80%, or preferably even of at least 90% is required.

Visser, H., et al., Arthritis and Rheumatism 46 (2002) 357-365, have proposed "A prediction model for persistent (erosive) arthritis". Their model consists of The developed prediction model consisted of 7 variables: symptom duration at first visit, morning stiffness for $\geq$1 hour, arthritis in $\geq$3 joints, bilateral compression pain in the metatarsophalangeal joints, rheumatoid factor positivity, anti-cyclic citrullinated peptide antibody positivity, and the presence of erosions (hands/feet). As can be seen two biochemical markers, RF and anti-CCP, formed part of their algorithm.

Recently, Meyer, O., et al. (Arthritis Research and Therapy 8/2 (2006) R40), have proposed to use serial determinations of anti-CCP autoantibodies to predict the radiological outcomes after five years of follow-up. They demonstrated that the determination of anti-CCP at baseline is not a sufficient predictor of disease progression. However an aid in the prediction of progression at baseline is exactly what is needed by the practitioner.

Whereas both RF and anti-CCP are important tools in establishing the diagnosis of RA, they appear to be not a strong aid in predicting the future course of disease. Many markers or sets of markers have been proposed, however the odds ratios achieved thus far have not been sufficient or have been based on a too large variety of biochemical and clinical parameters to meet clinical routine requirements.

Hence there is a tremendous need for a method, especially based on biochemical parameters, aiding in assessing whether an RA patient is at risk of disease progression or not.

It now has been surprisingly found that the two markers CRP and interleukin-6 supplement each other and thus lead to an improvement in the assessment of a patient's risk to undergo a more severe course of RA. The present invention is expected to at least partially overcome the problems existing in the field of assessing whether an RA patient is at risk of disease progression by providing methods and reagents for assessing whether an RA patient is at risk of disease progression in vitro.

SUMMARY OF THE INVENTION

The present invention is directed to a method aiding in assessing the risk of disease progression for a patient having rheumatoid arthritis (RA), the method comprising the steps of obtaining a liquid sample, measuring in said sample the concentration of both C-reactive protein (CRP) and interleukin-6, and of optionally one or more other marker, and correlating the concentrations determined for CRP and interleukin-6, and the optionally one or more other marker to the risk of disease progression.

Also disclosed is the use of a marker panel comprising at least CRP and interleukin-6 in assessing the risk of disease progression for a patient having RA.

Further the invention relates to a kit for performing the method aiding in assessing the risk of disease progression for a patient having rheumatoid arthritis as disclosed in the present comprising such kit comprising the reagents required to specifically measure CRP and interleukin-6, respectively, and optionally auxiliary reagents for performing the measurements.

Also disclosed is a protein array device comprising at least the appropriate specific binding partners for measurement of CRP and interleukin-6 and optionally appropriate specific binding partners for one or more other marker useful in assessing the risk of disease progression for a patient having rheumatoid arthritis.

BRIEF DESCRIPTION OF THE FIGURES

FIG. 2 Boxplots for CRP
Sensitivity=35%; total error=23%.
FIG. 3 Boxplots for IL-6
Sensitivity=35%; total error=25%.
FIG. 4 Boxplots for the marker combination CRP+IL-6
Sensitivity=50%; total error=20%.
FIG. 5 Boxplots for the marker combination CRP, IL-6 and pro-MMP3
Sensitivity=53%; total error=20%.

DETAILED DESCRIPTION OF THE INVENTION

Figure 1:
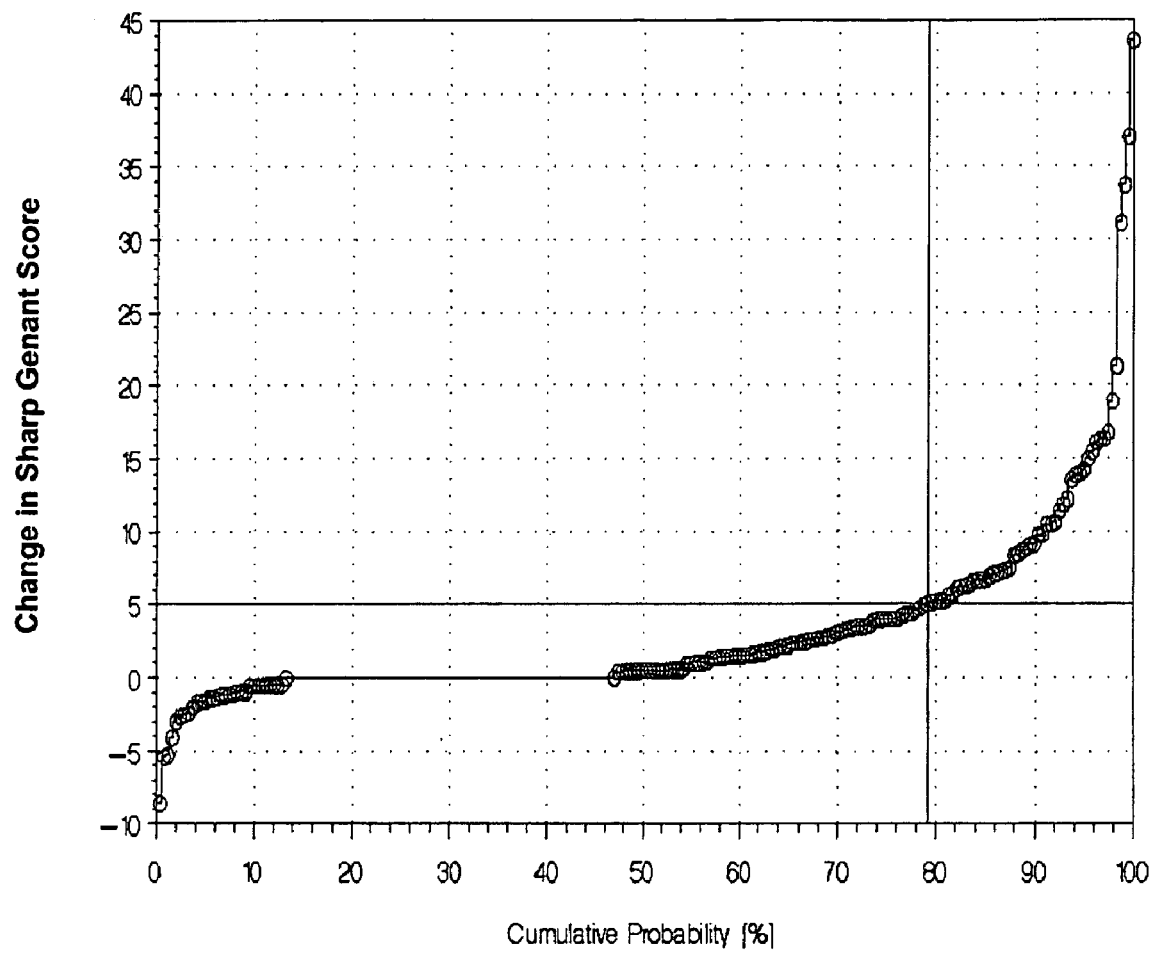
FIG. 1 Cumulative probability plot of progression rate 1 for all RA patients
(x-axis=cumulative probability %; y-axis=change in Sharp Genant Score)
Figure 2:
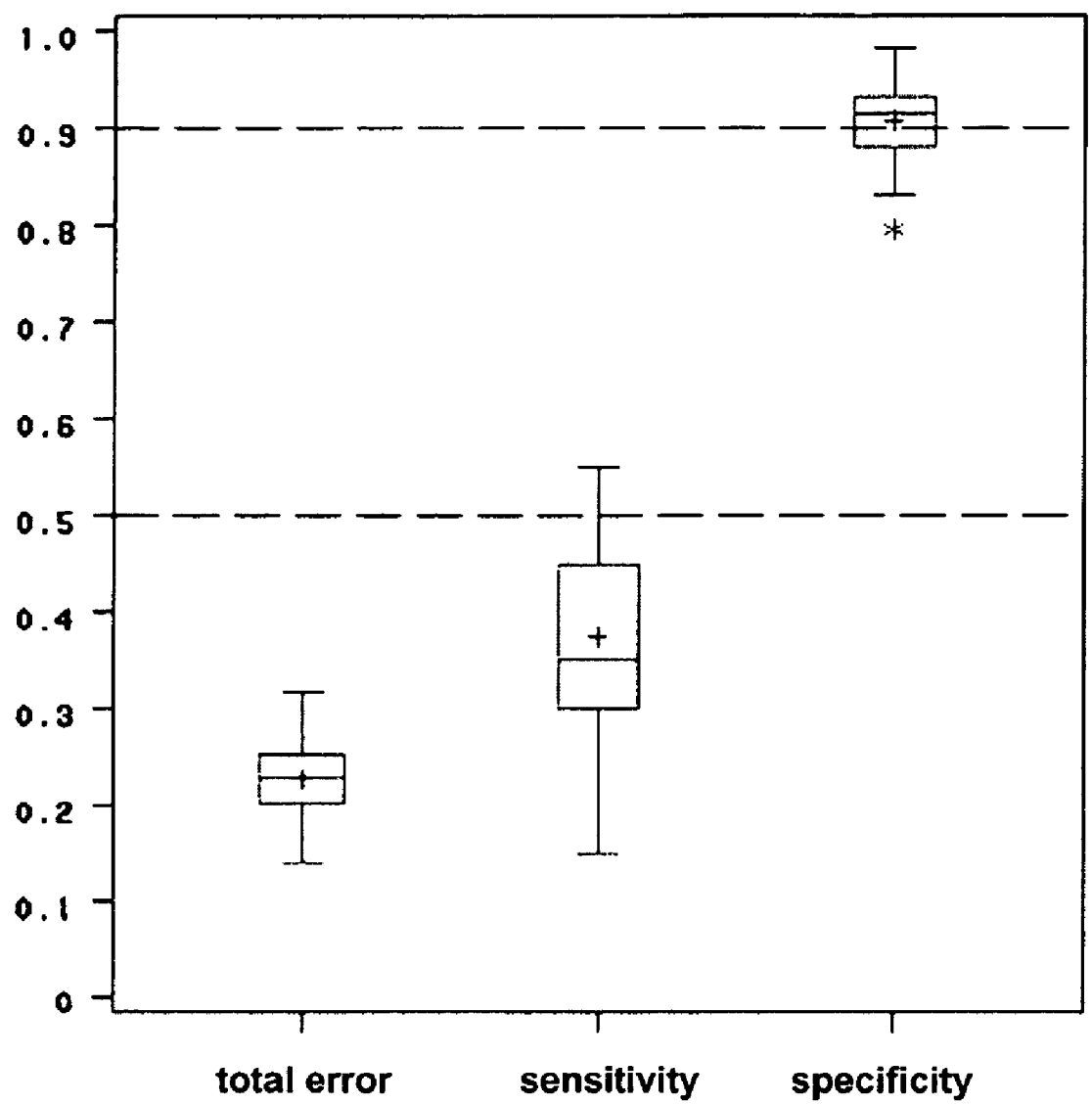
FIGS. 2 to 5 show boxplots of individual markers or marker combinations. RA patients of panel I have been classified as having disease progression or as having no disease progression. The specificity (right-hand box in each Figure) has been set to about 90% (=0.9 on the y-axis). The sensitivity for each marker or marker combination is shown in the middle box and the corresponding total error is shown by aid of the left-hand boxplot.
(boxes=$25^{th}$ to $75^{th}$ quartile; whiskers=1.5 times interquartile range; – in box=median; + indicates the position of the mean; *=individual value falling outside the whiskers)
Figure 3:
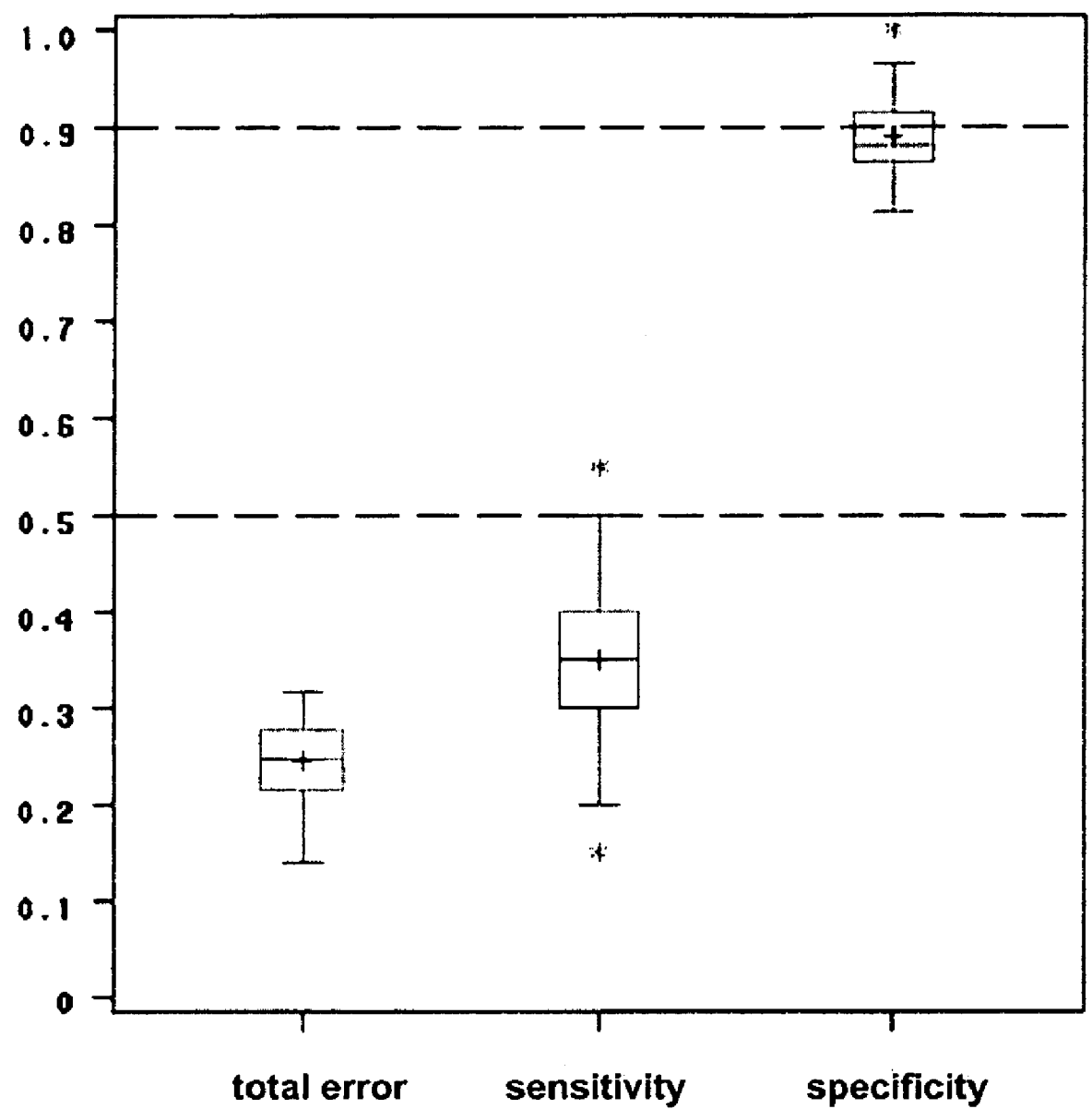
Figure 4:
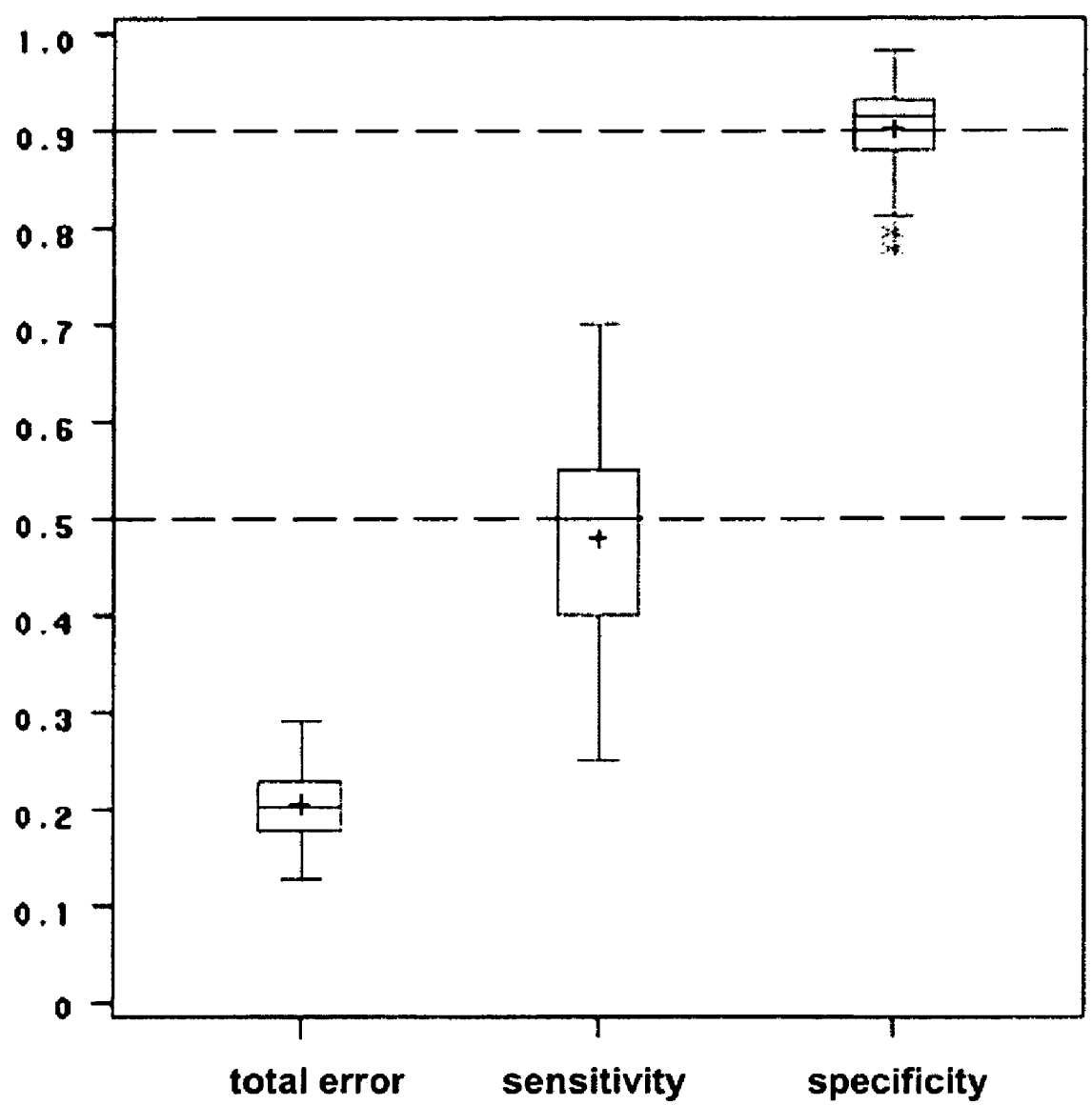
Figure 5:
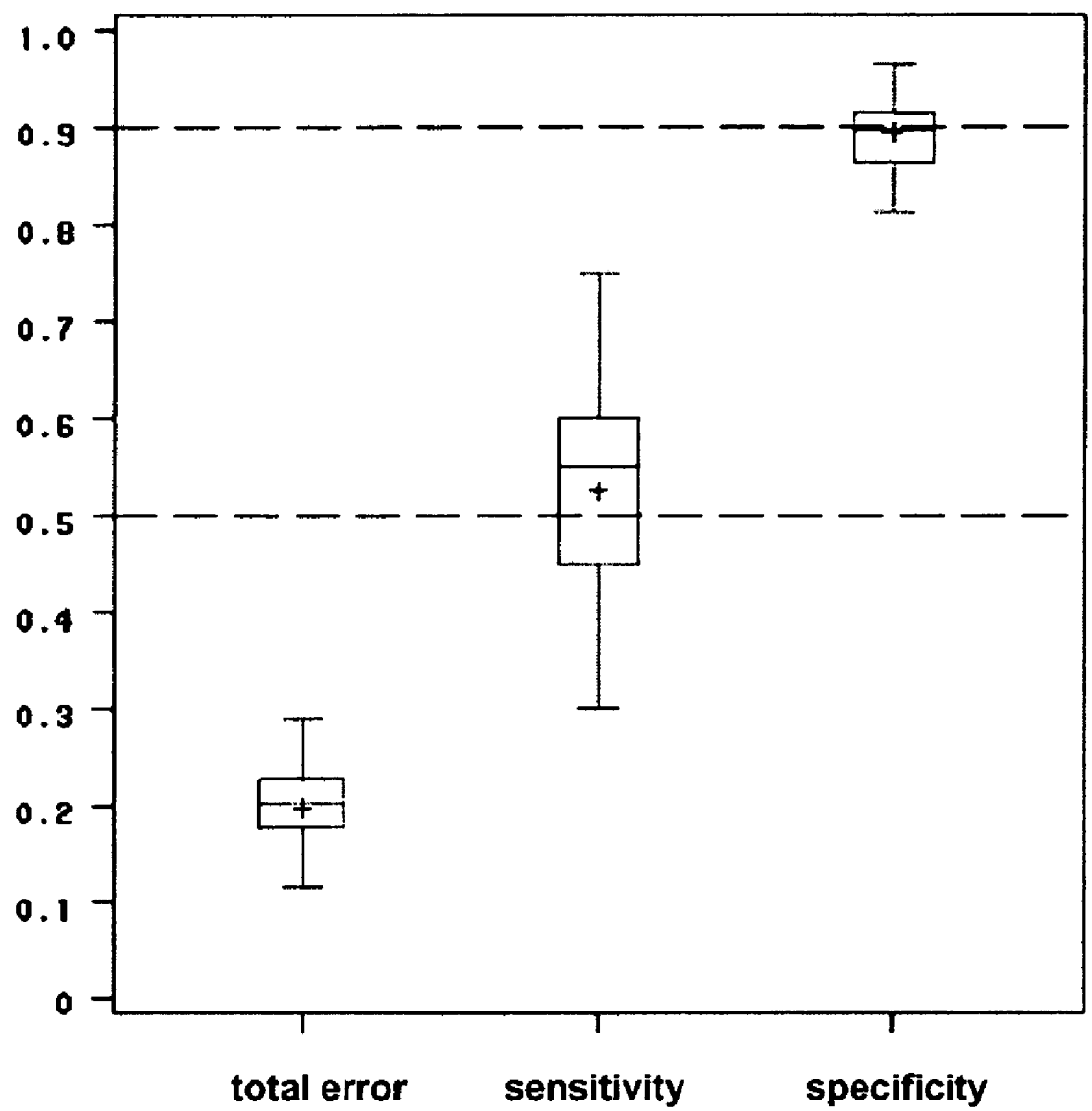

In a first preferred embodiment the present invention relates to a method aiding in assessing the risk of disease progression for a patient having rheumatoid arthritis (RA), the method comprising the steps of a) obtaining a liquid sample, b) measuring in said sample the concentration of both C-reactive protein (CRP) and interleukin-6, and of optionally one or more other marker, and c) correlating the concentrations determined in step (b) to the risk of disease progression.

As used herein, each of the following terms has the meaning associated with it in this section.

The articles "a" and "an" are used herein to refer to one or to more than one (i.e. to at least one) of the grammatical object of the article. By way of example, "a marker" means one marker or more than one marker.

The term "marker" as used herein refers to both biochemical as well as clinical markers. The terms marker and parameter are used interchangeable.

A "biochemical marker" or "biomarker" as used herein refers to a biomolecule to be used as a target for analyzing patient test samples. Examples of such molecular targets are nucleic acids, proteins or polypeptides themselves as well as antibodies present in a sample.

A "clinical marker" in the sense of the present invention refers to the standardized clinical assessment of an RA patient. Preferred clinical markers are scores like a disease activity score and/or a radiological score.

The proteins or polypeptides used as a marker in the present invention are contemplated to include any variants of said protein as well as fragments of said protein or said variant, in particular, immunologically detectable fragments as present in a patient's bodily fluid. One of skill in the art would recognize that proteins which are released by cells or present in the extracellular matrix which become damaged, e.g., during inflammation could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene, but differ in their PI or MW, or both (e.g., as a result of alternative mRNA or pre-mRNA processing, e.g. alternative splicing or limited proteolysis) and in addition, or in the alternative, may arise from differential post-translational modification (e.g., glycosylation, acylation, and/or phosphorylation).

The term marker, as indicated above, according to the present invention also relates to antibodies present in a sample. In the present case, i.e. in RA, these antibodies are autoantibodies. Autoantibodies are antibodies in a patient sample which bind to an antigen present in, or on, or produced by the patient's own cells.

The term "sample" as used herein refers to a biological sample obtained for the purpose of evaluation in vitro. In the methods of the present invention, the sample or patient sample preferably may comprise any body fluid. Preferred test samples include blood, serum, plasma, urine, saliva, and synovial fluid. Preferred samples are whole blood, serum, plasma or synovial fluid, with plasma or serum being most preferred. The sample is merely used for the in vitro diagnostic method of the invention and the remaining material of the sample is not transferred back into the patient's body. The sample is discarded once the analysis has been performed.

The term "aiding" in assessing the risk of disease progression is used to indicate that the method according to the present invention will (together with other variables, e.g., clinical parameters or the parameters disclosed in the dependent claims) aid the physician to assess the risk of disease progression for a patient having rheumatoid arthritis. The present invention relates to an in vitro method of assessing the risk of disease progression for a patient having rheumatoid arthritis (RA), the method comprising the steps of a) obtaining a liquid sample, b) measuring in said sample the concentration of both C-reactive protein (CRP) and interleukin-6, and of optionally one or more other marker, and c) correlating the concentrations determined in step (b) to the risk of disease progression. This method will be one of the components taken into consideration by the physician thereby helping i.e. aiding him to assess the risk of disease progression.

The terms "assessing the risk" or "or assessing the likelihood", e.g., of disease progression, are used to indicate that when practicing the method according to the present invention, the result will always indicate a relative risk or a relative likelihood of progressive RA. The higher the result the higher the relative risk of the RA patient to undergo a progressive course of disease.

"Disease progression" in the sense of the present invention is assessed by Sharp-Genant-Score. A patient with a progression rate >5 per year (change of the Sharp-Genant-Score from baseline after one or two years) is classified as an RA patient with disease progression. All other patients are classified as having no disease progression.

A "patient having rheumatoid arthritis" is a patient meeting the revised criteria developed for the classification of Rheumatoid Arthritis from the American Rheumatism Association (Arnett, F. C., et al., Arthritis Rheum. 31 (1988) 315-324). These criteria are herewith included by reference.

The inventors of the present invention have defined two sub-groups of RA patients, one showing disease progression and a reference population or sub-group of RA showing no disease progression and investigated the potential of biochemical markers for predicting disease progression based on these patient cohorts.

Surprisingly it could be found and established that the marker combination of CRP plus interleukin-6 is key for improving the sensitivity of prediction of the disease course for an RA patient at the clinically required high specificity.

In a method according to the present invention at least the concentration of the biomarkers CRP and IL-6, respectively, is determined and this marker combination is correlated to the risk of disease progression for a patient diagnosed with RA.

As the skilled artisan will appreciate the step of correlating a marker level to a certain likelihood or risk can be performed and achieved in different ways. Preferably the values measured for the markers CRP and IL-6, are mathematically combined and the combined value is correlated to the underlying diagnostic question. Marker values may be combined by any appropriate state of the art mathematical method.

Preferably the mathematical algorithm applied in the combination of markers is a logistic function. The result of applying such mathematical algorithm or such logistical function preferably is a single value. This value can easily be correlated to the risk of RA disease progression. In a preferred way such logistic function is obtained by a) classification of RA patients into the groups of patients undergoing disease progression and the group of patients not undergoing disease progression, b) identification of markers which differ significantly between these groups by univariate analysis, c) logistic regression analysis to assess the independent discriminative values of markers useful in assessing RA disease progression and d) construction the logistic function to combine the independent discriminative values.

In a preferred embodiment the logistic function used for combining the values for CRP and IL-6 is obtained by a) classification of RA patients into the groups of patients undergoing disease progression and of patients not undergoing disease progression, respectively, b) establishing the values for CRP and interleukin-6 c) performing logistic regression analysis and d) construction the logistic function to combine the marker values for CRP and interleukin-6.

In a further preferred embodiment the logistic function for combining the measurements of CRP and IL-6 with the values for one or more other marker is obtained by a) classification of RA patients into the groups of patients undergoing disease progression and the group of patients not undergoing disease progression, b) identification of one or more additional marker which differentiates significantly between these groups by univariate analysis, c) performing logistic regression analysis to assess if said marker has additive discriminative value over the combination of CRP and interleukin-6 in assessing RA disease progression and d) constructing the logistic function to combine the values measured for CRP, interleukin-6 and the one or more additional marker.

A logistic function for correlating a marker combination to a disease preferably employs an algorithm developed and obtained by applying statistical methods like, Discriminant analysis (DA) (i.e. linear-, quadratic-, regularized-DA), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. The skilled artisan will have no problem in selecting an appropriate statistical method to evaluate a marker combination of the present invention and thereby to obtain an appropriate mathematical algorithm. Preferably the statistical method employed to obtain the mathematical algorithm used in correlating the marker combination of the invention to the risk of disease progression of RA is selected from DA (i.e. Linear-, Quadratic-, Regularized Discriminant Analysis), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting Methods), or Generalized Linear Models (i.e. Logistic Regression). Details relating to these statistical methods are found in the following references: Ruczinski, I., et al., J. of Computational and Graphical Statistics 12 (2003) 475-511; Friedman, J. H., J. of the American Statistical Association 84 (1989) 165-175; Hastie, T., et al., The Elements of Statistical Learning, Springer Verlag (2001); Breiman, L., et al., Classification and regression trees, California, Wadsworth (1984); Breiman, L., Random Forests, Machine Learning 45 (2001) 5-32; Pepe, M. S., The Statistical Evaluation of Medical Tests for Classification and Prediction, Oxford Statistical Science Series, 28 (2003); and Duda, R. O., et al., Pattern Classification, Wiley Interscience, 2nd edition (2001).

It is a preferred embodiment of the invention to use an optimized multivariate cut-off for the underlying combination of biological markers and to discriminate state A from state B, e.g. RA disease progression from no RA disease progression, respectively. In this type of analysis the markers are no longer independent but form a marker panel. It could be established that combining the measurements of CRP and of IL-6 does significantly improve the diagnostic accuracy in assessing the risk of disease progression for a patient having RA.

In univariate analysis CRP, IL-6 and several other markers have an area under the curve (AUC) of about 0.7 to about 0.8. Both CRP and IL-6 are inflammation markers and they are highly correlated to each other. It is therefore quite unexpected to see that CRP and IL-6 can be combined and at the same level of specificity as the individual markers show a tremendous improvement in sensitivity.

The AUC is an indicator of the performance or accuracy of a diagnostic procedure. Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed. The area under the ROC plot is called AUC.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or disease progression versus no disease progression.

In each case, the ROC plot depicts the overlap between the two distributions by plotting the sensitivity versus 1-specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1-specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot (AUC). By convention, this area is always $\geq 0.5$ (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

The overall assay sensitivity will depend on the specificity required for practicing the method disclosed here. In certain preferred settings a specificity of 75% may be sufficient and statistical methods and resulting algorithms can be based on this specificity requirement. In further preferred embodiments the method used to assess the risk of disease progression for a patient having RA will be based on a specificity of 80%, 85%, or especially preferred 90% or 95%. As obvious from the Examples section, the marker combination employing CRP and IL-6 at a specificity of 90% has a good sensitivity of about 50%. This compares to a total error of about 20% and is better than the total error achieved with state of the art approaches solely based on individual biochemical markers.

The levels given for CRP and IL-6 in the examples section have been measured and established with the assay procedures given there. It has to be understood that different assays may lead to different cut-off values. The skilled artisan will have no problems in establishing such supplier-dependent cut-off values by following the procedures outlined in the present invention.

Interleukin-6 (IL-6) is a 21 kDa secreted protein that has numerous biological activities that can be divided into those involved in hematopoiesis and into those involved in the activation of the innate immune response. IL-6 is an acute-phase reactant and stimulates the synthesis of a variety of proteins, including adhesion molecules. Its major function is to mediate the acute phase production of hepatic proteins, and its synthesis is induced by the cytokines IL-1 and TNF-α. IL-6 is normally produced by macrophages and T lymphocytes. The normal serum concentration of IL-6 is <5 pg/ml.

Preferred means of detecting biomarkers like CRP and IL-6 are specific binding assays, especially immunoassays. Immunoassays are well known to the skilled artisan. Methods for carrying out such assays as well as practical applications and procedures are summarized in related textbooks.

Examples of related textbooks are Tijssen, P., In: Practice and theory of enzyme immunoassays, eds. R. H. Burdon and v. P. H. Knippenberg, Elsevier, Amsterdam (1990), pp. 221-278, and various volumes of Methods in Enzymology, eds. Colowick, S. P., and Caplan, N. O., Academic Press, dealing with immunological detection methods, especially volumes 70, 73, 74, 84, 92 and 121.

IL-6 for example can be measured by a competitive type or a sandwich type immunoassay. IL-6 preferably is measured in a sandwich immunoassay which is essentially based on an antibody specifically binding to IL-6 which is directly or indirectly bound or capable of binding to a solid phase, an antibody specifically binding to IL-6 which is detectably labeled, and incubating these reagents under conditions allowing for binding of the anti-IL-6 antibodies to IL-6 in a sample, separating unbound detectably labeled antibody, determining the amount of labeled antibody bound via IL-6, and correlating the amount of labeled antibody bound to the concentration of IL-6 in the sample.

C-reactive protein (CRP) is a homopentameric $Ca^{2+}$-binding acute phase protein with 21 kDa subunits that is involved in host defense. CRP synthesis is induced by IL-6, and indirectly by IL-1, since IL-1 can trigger the synthesis of IL-6 by Kupffer cells in the hepatic sinusoids. The normal plasma concentration of CRP is <3 µg/ml (30 nM) in 90% of the healthy population, and <10 µg/ml (100 nM) in 99% of healthy individuals. Plasma CRP concentrations can, e.g. be measured by homogeneous assay formats or ELISA. CRP is considered a marker of systemic inflammation.

A factor further confounding and complicating the risk assessment of disease progression for a patient having RA is the fact that patients at the time of visit may be at different stages of disease development and under various treatment regimens. The inventors of the present invention have been able to demonstrate that marker combination found is predictive for both patients not yet treated with an anti-rheumatic drug and for patients already under treatment with a disease modifying anti-rheumatoid drug (DMARD). Especially the later finding is of great relevance, it indicates that the method disclosed in the present invention may be of aid in identifying those patients not responding or not sufficiently responding to treatment with a DMARD. In a preferred embodiment the method according to present invention is practiced using a sample obtained from an RA-patient who is under treatment with an anti-rheumatic drug selected from group of disease modifying anti-rheumatoid drugs (DMARDs). Also preferred, the method disclosed herein is practiced using a sample obtained from an RA-patient who has not been under treatment with an anti-rheumatic drug.

It is believed that with the identification of the marker combination CRP and IL-6 the key marker combination useful in assessing the risk of disease progression for a patient having RA has no been identified. As has been further shown by the inventors the method of assessing the risk of disease progression for a patient having RA can be further improved by combining the measurement of the two key markers CRP and IL-6 with further parameters. In a further preferred embodiment the present invention relates to a method comprising the steps of a) obtaining a liquid sample, b) measuring in said sample the concentration of both C-reactive protein (CRP) and interleukin-6, and of one or more other marker, and c) correlating the concentrations determined in step (b) to the risk of disease progression, wherein the optionally one or more other marker is selected from the group consisting of bone or cartilage markers, synovial fluid markers, other inflammation markers, genetic markers and radiological scores.

In a preferred embodiment the one or more other marker used in a method according to the present invention is a bone or cartilage marker, preferably said bone or cartilage marker is selected from the group consisting of PINP, β-CrossLaps, CartiLaps, osteocalcin and ICTP also preferred the one or more bone or cartilage marker is ICTP or/and CartiLaps.

The most prominent joint tissues are bone, cartilage and the synovium. Since rheumatoid arthritis is a destructive disease these tissues will be most affected. They are a likely source of potential biological markers in the field of RA. In principle these markers may come not only from the destruction of the respective tissue but also from a deregulated and/or ineffective repair process. The experienced artisan will understand that markers of bone, cartilage or synovium metabolism can originate either from synthesis or from destruction of these tissues. The various markers of bone, cartilage and/or synovium metabolism can be delineated from two different groups of proteins. They come either from the numerous types of collagen or from non-collagenous proteins. Non-collagenous proteins are often involved in the formation of the extracellular matrix. Some of these markers can be found in all three tissues in varying amounts.

Bone and/or cartilage markers include markers of both markers of bone and/or cartilage collagen degradation as well as markers of bone and/or cartilage collagen formation. Preferred collagen-derived bone or cartilage markers are:

1. Pyridinoline (=PYD), deoxy-pyridinoline (=DPD) and Glc-Gal-PYD: Pyridinoline (=PYD) stabilizes collagen by cross-linking the strands of the collagen triple helix. The chemical structure of PYD is very stable and can be found in serum and urine as an end product of collagen degradation (Knott, L., and Bailey, A. J., Bone 22 (1998) 181-187). It has been linked to arthritis (Kaufmann, J., et al., Rheumatology 42 (2003) 314-320). PYD monitors cartilage involvement of joint destruction since it is released from cartilage and only to some degree from bone while its close cousin deoxy-pyridinoline (=DPD) originates mostly from bone. All three markers have been linked to arthritis (Kaufmann, supra). The glycosylated form Glc-Gal-PYD has mostly been found in synovial tissue (Gineyts, E., et al., Rheumatology 40 (2001) 315-323).

2. Cross-linked telopeptides: CTX-I, CTX-II, NTX-I and the LQ-epitope which are cross-linked telopeptides either from the C- or N-terminus of collagens type I or type II, respectively, and of which β-CTX-I is also known as β-CrossLaps® (Bonde, M., et al., Clin. Chem. 40 (1994) 2022-2025).

3. Type I collagen carboxyterminal telopeptide (=ICTP) refers to a fragment and marker of type I collagen which originally has been derived from type I collagen by cyanobromide cleavage (U.S. Pat. No. 5,538,853).

4. Linear peptides derived from collagen: The assay termed Cartilaps® measures a linear peptide that is derived from the C-terminal region of collagen type II (U.S. Pat. No. 6,372,442).

5. Modified amino acids: Collagen comprises modified amino acids like hydroxyproline and galactosyl hydroxylysine which may be used as a marker of collagen break-down (Al-Dehaimi, A. W., et al., Clin. Chem. 45 (1999) 676-681).

6. Collagen neoepitopes: Col2-3/4 and CIIN are neoepitopes generated by the initial cleavage of collagen II by collagenases (Billinghurst, R. C., et al., J. Clin. Invest. 99 (1997) 1534-1545).

7. Collagen markers considered reflecting bone formation: The N-terminal as well as the C-terminal pro-peptide of type I collagen (=PINP and PICP), respectively, are clipped from the precursor polypeptide (procollagen) during/after synthesis and considered markers of bone formation. PIICP is the corresponding pro-peptide from collagen type II, whereas PIIINP is derived from collagen III.

Also preferred the bone or cartilage marker be a non-collagenous marker, like: CS846, which is a chondriotin sulfate epitope created during aggrecan synthesis; cartilage oligomeric matrix protein (=COMP) that has bridging functions in cartilage (Saxne, T., and Heinegard, D., Br. J. Rheumatol. 31 (1992) 583-591); cartilage intermediate layer protein (=CILP), which is a matrix protein of cartilage (Lorenzo, P., et al., J. Biol. Chem. 273 (1998) 23463-23468); cartilage matrix proteins 1-3 also known as matrilins; chondromodulins that act as signaling molecules in cartilage (Suzuki, F., Connect. Tissue Res. 35 (1996) 303-307); cartilage derived retinoic acid-sensitive protein (=CD-RAP) or MIA, which has a yet to be defined function in chondrocyte modulation (Mueller-Ladner, U., et al., Rheumatology 38 (1999) 148-154); osteocalcin, which is synthesized by osteoblasts, belongs to the major non-collagen matrix protein of bone and is used to monitor bone turnover (Gundberg, C. M., et al., J. Clin. Ligand Assay 21 (1998) 128-138); and the bone sialoproteins, which are major non-collagen matrix proteins of bone, such as bone sialoprotein II, now known as bone sialoprotein, which e.g., has been evaluated as marker for bone turn-over (Saxne, T., et al., Arthritis Rheum. 38 (1995) 82-90).

In a preferred embodiment the one or more other marker used in a method according to the present invention is a synovial marker selected from the group consisting of matrix metalloprotease 1 (=pro-MMP-1), matrix metalloprotease 3 (=pro-MMP 3), hyaluronic acid, preferably the one or more other synovial marker is hyaluronic acid or and pro-MMP 3.

The family of matrix-metalloproteinases (=MMPs) degrades almost all components of the extra-cellular matrix. Hence MMPs have been related to various types of cancer but also to inflammatory processes in RA. MMP 1 and MMP 3 are produced by fibroblasts, osteoblasts and endothelial cells upon stimulation by pro-inflammatory cytokines like IL-1 or TNF-α. Generally MMPs are found in the circulation as inactive pro-form, i.e., pro-MMP 1 and pro-MMP 3, respectively. pro-MMP 1 and pro-MMP 3 have been detected in synovial fluid of RA-patients and their levels are responsive to anti-TNF-α therapy. The most preferred metalloprotease to be used in marker panel for assessing the risk of disease progression for a patient having RA is pro-MMP 3.

Instead of the metalloproteinases mentioned above it is also possible to used their corresponding inhibitors collectively referred to as tissue inhibitors of matrix metalloproteinases (=TIMPs), e.g. MMP-1 and MMP-3 are in vivo inactivated by TIMP-1 asialoglycoprotein of 29.5 kD that forms a 1:1 stoichiometric complex with the MMPs. The relation of TIMP-1 and TIMP-2 to the destruction of cartilage has been investigated in RA (Ishiguro, N., et al., Arthritis Rheum. 44 (2001) 2503-2511).

The glycosaminoglycan hyaluronic acid is one of the macromolecules essential for the function of a joint. It is synthesized by fibroblasts and other specialized connective tissue cells. Hyaluronic acid is involved in formation of the extracellular matrix and in cell to cell contacts. High concentrations are found in synovial fluid where it is responsible for the retention of water thereby contributing to the lubrication of joints. In rheumatoid arthritis the synthesis of hyaluronic acid is stimulated by the proinflammatory mediators IL-1 and TNF-α leading to increase serum/plasma levels (Sawai, T., and Uzuki, M., Connective Tissue 33 (2001) 253-259).

In a preferred embodiment the one or more other marker used in a method according to the present invention is a genetic marker selected from the group consisting of an HLA-DR4 and an HLA-DRB1 allele, preferably the one or more other genetic marker is an HLA-DRB1*01 or/and an HLA-DRB1*04 allele (Goronzy, J. J., et al., Arthritis and Rheumatism 50 (2004) 43-54).

In a preferred embodiment the one or more other marker used in a method according to the present invention is a radiological score, preferably said radiological score is selected from the group consisting of Sharp-score, Sharp-Genant-score, van der Heijde-Sharp-score, Ratingen-score, Larsen-score, RAU-score and Herborn-score also preferred the one or more radiological score is the Sharp-Genant-score, or/and the Larsen-score.

The "Sharp-score" has first been introduced in 1971 (Sharp, J. T., et al., Arthritis and Rheumatism 14 (1971) 706-720) and has been further elucidated in 1985 (Sharp, J. T., et al., Arthritis and Rheumatism 28 (1985) 1326-1335).

The "Sharp-Genant-score" is a modification of the Sharp-score as proposed by Genant in 1983 (Genant, H. K., Am. J. Med. 75 (1983) 3547).

The "van der Heijde-Sharp-score" is a modification of the Sharp-score as proposed by van der Heijde in 1989 (van der Heijde, D. M. F. M., Lancet 1 (1989) 1036-1038).

The "Larsen-score" has first been introduced in 1977 (Larsen, A., et al., Acta Radiol. Diagn. 18 (1977) 481-491). The "RAU-score" sometimes also referred to as "Ratingen-score" is a modification of the Larsen-score (Rau, R. and Wassenberg, S., Z. Rheumatol. 62 (2003) 555-565).

In a preferred embodiment the one or more other marker used in a method according to the present invention is a further marker of inflammation preferably said further marker of inflammation is an inflammation marker selected from the group consisting of S100-proteins, erythrocyte sedimentation rate (ESR), SAA and E-selectin preferably it is SAA or/and E-selectin.

The term "other marker of inflammation" or "further marker of inflammation" is used to indicate that these marker are neither CRP nor IL-6.

Serum amyloid A (=SAA) is an acute phase protein of low molecular weight of 11.7 kDa. It is predominantly synthesized by the liver in response to IL-1, IL-6 or TNF-α stimulation and is involved in the regulation of the T-cell dependent immune response. Upon acute events the concentration of SAA increases up to 1000-fold reaching one milligram per milliliter. It is used to monitor inflammation in diseases as divers as cystic fibrosis, renal graft refection, trauma or infections. In rheumatoid arthritis is has in certain cases been used as a substitute for CRP, but, SAA is not yet as widely accepted.

S100-proteins form a constantly increasing family of $Ca^{2+}$-binding proteins that today includes more than 20 members. The physiologically relevant structure of S100-proteins is a homodimer but some can also form heterodimers with each other, e.g. S100A8 and S100A9. The intracellular functions range from regulation of protein phosphorylation, of enzyme activities, or of the dynamics of the cytoskeleton to involvement in cell proliferation and differentiation. As some S100-proteins are also released from cells, extracellular functions have been described as well, e.g., neuronal survival, astrocyte proliferation, induction of apoptosis and regulation of inflammatory processes. S100A8, S100A9, the heterodimer S100A8/A9 and S100A12 have been found in inflammation with S100A8 responding to chronic inflammation, while S100A9, S100A8/A9 and S100A12 are increased in acute inflammation. S100A8, S100A9, S100A8/A9 and S100A 12 have been linked to different diseases with inflammatory components including some cancers, renal allocraft rejection, colitis and most importantly to RA (Burmeister, G., and Gallacchi, G., Inflammopharmacology 3 (1995) 221-230; Foell, D., et al., Rheumathology 42 (2003) 1383-1389). The most preferred S100 markers for use in a marker panel for assessing disease progression in RA according to the present invention are S100A8, S100A9, S100A8/A9 heterodimer and S100A12. sE-selectin (soluble endothelial leucocyte adhesion molecule-1, ELAM-1) is a 115 kDa, type-I transmembrane glycoprotein expressed only on endothelial cells and only after activation by inflammatory cytokines (IL-1β, TNF-α) or endotoxin. Cell-surface E-selectin is a mediator of the rolling attachment of leucocytes to the endothelium, an essential step in extravasion of leucocytes at the site of inflammation, thereby playing an important role in localized inflammatory response. Soluble E-selectin is found in the blood of healthy individuals, probably arising from proteolytic cleavage of the surface-expressed molecule. Elevated levels of sE-selectin in serum have been reported in a variety of pathological conditions (Gearing, A. J. H., et. al., Annals N.Y. Acad. Sci. 667 (1992) 324-331).

Preferably the one or more other marker used in combination with CRP and IL-6 in order to assess the risk of disease progression in RA is a biochemical marker or a biomarker. Preferably the biomarker is a polypeptide or an autoantibody.

It is obvious from the Examples section that a marker panel comprising CRP and IL-6 will aid in assessing the risk of disease progression for a patient having RA. In a further embodiment the invention relates to the use of a marker panel comprising at least CRP and interleukin-6 in assessing the risk of disease progression for a patient having rheumatoid arthritis.

The one or more additional marker used together with CRP and IL-6 preferably is or are also part of a marker panel, i.e., a series of markers appropriate to further refine any assessing of the risk of disease progression for a patient having RA. The total number of markers in such an marker panel for assessing RA progression is preferably less than 20 markers, more preferred less than 15 markers, also preferred are less than 10 markers with 8 or less markers being even more preferred. Preferred are marker panels for assessing disease progression in RA comprising 3, 4, 5, or 6 markers in total.

A further preferred embodiment relates to the use of a marker panel in assessing of the risk of disease progression for a patient having RA the panel comprising CRP, interleukin-6 and at least one additional marker selected from the group consisting of CartiLaps, hyaluronic acid, E-selectin and ICTP.

In a preferred embodiment the marker panel aiding in assessing of the risk of disease progression for a patient having RA comprises CRP, interleukin-6 and hyaluronic acid.

In a preferred embodiment the marker panel aiding in assessing of the risk of disease progression for a patient having RA comprises CRP, interleukin-6 and E-selectin.

In a preferred embodiment the marker panel aiding in assessing of the risk of disease progression for a patient having RA comprises CRP, interleukin-6 and ICTP.

In a preferred embodiment the marker panel aiding in assessing of the risk of disease progression for a patient having RA comprises CRP, interleukin-6 and CartiLaps.

In a further preferred embodiment the reagents required to perform the measurements for at least CRP and interleukin-6 are provided as kit. Thus the invention also relates to a kit comprising the reagents required to specifically measure CRP and interleukin-6, respectively, and optionally auxiliary reagents for performing the measurements.

In a preferred embodiment of the invention the reagents that specifically bind to the two biomarker proteins CRP and IL-6 and to the optionally one or more other biomarkers are immobilized on a solid support such as for example a polystyrene surface. A preferred embodiment of the invention provides a protein microarray or protein array device for the simultaneous binding and quantification of the marker panel used to assess disease progression in RA. The protein array device consists of molecules (capture agents) bound to a defined spot position on a support material. Preferably biotinylated specific binding reagents are bound as very small spots onto a solid phase that is coated with streptavidin. The array is then exposed to the sample. Capture agents such as antibodies are able to bind the protein of interest from the biological sample. The binding of the specific analyte proteins to the individual spots can then be monitored by quantifying the signal generated by each spot.

In yet a further preferred embodiment the present invention relates to a protein array device comprising at least the appropriate specific binding partners for measurement of CRP and interleukin-6 and optionally appropriate specific binding partners for one or more other marker useful in assessing the risk of disease progression for a patient having rheumatoid arthritis.

The following examples and figures are provided to aid the understanding of the present invention, the true scope of which is set forth in the appended claims. It is understood that modifications can be made in the procedures set forth without departing from the spirit of the invention.

EXAMPLE 1

Study Population

Samples derived from 237 highly characterized RA patients with maximum disease duration of 15 years were collected in five European centers with a follow-up of one or two years. All individuals were diagnosed as RA-patients according to the 1987 revised criteria for the classification of Rheumatoid Arthritis from the American Rheumatism Association (Arnett, F. C., et al., Arthritis Rheum. 31 (1988) 315-324). All patients were documented with an extensive case report form (=CRF). The CRF included the Health Assessment Questionnaire, the SF36 Questionnaire, swollen and tender joint count, laboratory parameters, clinical history of relevant surgery, medication, co-morbidities and medication for co-morbidities. X-rays were taken from hands and feet at baseline, after one and after 2 years following a standardized procedure. Only the baseline samples obtained from the RA-patients were used in the measurement of the different analytes and the corresponding results were used for the univariate and multi-variate analysis.

Demographic data for the study population are given in Table 1.

TABLE 1

| RA-patient collective | |
|---|---|
| Number RA-patients | 237 |
| Patients with all x-rays (BL, 1 year, 2 years) | 204 |
| Patients with x-rays at BL and year 1 | 33 |
| Age (mean, (minimum/maximum)) | 58.6 (18-87) |
| Gender distribution (male/female) | 84/153 |
| Erosiveness at baseline (erosive/non-erosive) | 155/82 |
| Disease duration (mean, (minimum/maximum)) | 4.9 (0.1-15.2) years |

EXAMPLE 2

Determination of the Sharp-Genant-Scores

From each patient x-rays were taken from hands and feet at baseline and after one and two years. The conventional film radiographs were sent to Synarc (Synarc GmbH, Hamburg, Germany), where the hard copy films were digitized using a Lumiscan 200 high resolution digitizer. After quality check each image was read by an experienced radiologist and scored according the Genant-modified Sharp scoring.

Morphological Scoring of Radiographs

Bone erosions and joint space narrowing in the hands and feet were scored according to a Genant-modified Sharp grading scheme as described below. This grading scheme is based on the Genant-modified Sharp scoring technique.

Erosion Score Fourteen sites in each wrist and hand (four proximal interphalangeal and five metacarpophalangeal joints, the carpometacarpal joint of the thumb, the scaphoid bone, the distal radius and the distal ulna) and six joints in each foot (five metatarsophalangeal joints and the interphalangeal joint of digit I (i.e., the great toe)) are scored using an eight-point scale from 0 to 3.5 based on the size of erosions and the area of bone (both sides of joint) involved:

0 (normal: no erosions)
0.5 (subtle loss of cortical continuity or equivocal findings of bone erosion)
1.0 (mild: definite but small erosions of one or both articular bones, usually at the bare areas, involving <25% of the articular surfaces)
1.5 (mild to moderate: small-medium erosions involving <25% of the articular bones of one or both articular bones)
2.0 (moderate: medium-large erosions involving approx. 26%-50% of the articular surface of both articular bones)
2.5 (moderate to severe: erosions of approx. 51%-75% of the articular surfaces)
3.0 (severe: erosions of approx. 76%-90% of the articular surfaces)
3.5 (very severe: erosions of 100% of the articular surfaces (total destruction of the articular surfaces)

Joint space narrowing (JSN) score. Thirteen sites in each wrist and hand (proximal interphalangeal joints of digits II to V, the interphalangeal joint of the thumb and five metacarpophalangeal joints, carpometacarpal joints of digits III-V as a single unit, the pericapitate (scaphoid-capitate and lunate-capitate combined) space and the radiocarpal joint) and six sites in each foot (five metatarsophalangeal joints and the interphalangeal joint of digit I (i.e., the great toe)) are scored using a nine-point scale from 0 to 4:

0 (normal)
0.5 (subtle joint space narrowing or equivocal findings)
1.0 (mild joint space narrowing (focal or minor))
1.5 (mild to moderate joint space narrowing)
2.0 (moderate joint space narrowing)
2.5 (moderate to severe joint space narrowing)
3.0 (severe joint space narrowing)
3.5 (severe joint space narrowing close to ankylosis)
4.0 (definite ankylosis)

Hands/wrists: The individual joint scores will be summed separately to create a total erosion score and a total JSN score for the hands/wrists. The maximum total erosion score for the hands/wrists is (14×3.5 maximum per joint)×2=98. The maximum total JSN score is (13×4 maximum per joint)×2=104. To provide equal weight to erosions and joint space narrowing, each sum is normalized to a scale of 0-100. If E-score is the sum of erosion scores and J-score is the sum of JSN scores for both hands, the normalized scores are calculated as follows:

normalized E-score=(E-score/98)×100, and normalized J-score=(J-score/104)×100.

Feet: As for the hands/wrists the individual joint scores will be summed separately to create a total erosion score and a total JSN score for the feet. The maximum total erosion score for the feet is (6×3.5 maximum per joint)×2=42. The maximum total JSN score is (6×4 maximum per joint)×2=48.

To provide equal weight to erosions and joint space narrowing, each sum will be normalized to a scale of 0-45. If E-score is the sum of erosion scores and J-score is the sum of JSN scores for both feet, the normalized scores are calculated as follows:

normalized E-score=(E-score/42)×45, and normalized J-score=(J-score/48)×45.

Combination: The Total score for the hands/wrists and feet is the sum of the individual totals for each. Thus the maximum score achievable is 290.

Erosion score=normalized E-score hands/wrists+normalized E-score feet, plus

JSN score=normalized J-score hands/wrists+normalized J-score feet, plus

Total score=Erosion score+JSN score.

The change in total scores is calculated as:

Erosion Change=(Follow-up Erosion score)−(Initial Erosion score) plus

JSN Change=(Follow-up JSN score)−(Initial JSN score), plus

Total Change=(Follow-up Total score)−(Initial Total score).

EXAMPLE 3

Classification of Patients in RA with Disease Progression and RA with No Disease Progression There are some possibilities discussed in the literature for classification of disease progression. Beside the ACR and EULAR criteria, which are mostly used in pharmaceutical studies for assessing treatment response also the IIAQ score and the radiological scores can be used for classification of disease progression. The most preferred methodology is the use of the change of any radiological score after one year. We decided to use the total Sharp-Genant-Score and to determine the individual change of this score one or two years after the baseline value (=progression rate).

Progression rate (1)=change of Sharp-Genant-Score (SGS) from baseline to year 1.

Progression rate (2)=change of Sharp-Genant-Score (SGS) from baseline to year 2.

The next important step was to define a cut-off value for the progression rates to be able to classify the patients in RA with progression and RA without progression. Therefore a cumulative probability plot of the progression rate 1 or 2 from all patients were made (see FIG. 1) (van der Heijde et al., Arthritis Rheum. 52 (2005) 49-60). Laying a straight line onto the first slope of the plot, the intersection point was determined at a progression rate (1) of "5". The same results was obtained using a probability plot of the progression rate (2). To use a progression rate of "5" (i.e. an increase in SGS of more than 5 per year) as a cut-off value for classification of RA patients into patients with or without progression was supported by following two arguments:
1. Using a progression rate (1) of "5" as cut-off value, approx. 20% of the RA patients of this sample collective will be classified as RA patients with progression.
2. The value of any scoring method used to measure a clinical outcome depends on its reliability. There are described different methods for the determination of the "sensitivity to change" (Boini, S. and Guillemin, F., Ann. Rheum. Dis. 60 (2001) 817-827). The best reliability score for classification of individual patients is the smallest detectable difference (SDD). The experts evaluating the radiographs used in establishing an SGS have determined a SDD of 5.1 for the SGS. This means, an SGS-change of about 5 is the minimal difference of one patients at two time points, which can be significantly discriminated.

Therefore the following classification was used:
Progression rate (1) or (2)>5: RA patient with progressive disease
Progression rate (1) or (2)≦5: RA patient with no progressive disease Using this definition we achieved following classification:
RA patients with disease progression: 59 patients
RA patients with no disease progression: 178 patients

EXAMPLE 4

Markers Measured

Table 2 represents the assays used and gives the test format as well as the suppliers of the assays. Most of the assays were manual microtiter plate (=MTP) format ELISAs. RF and CRP were determined in a homogeneous test format on an automatic Hitachi analyzer. All marker concentrations were determined in serum samples with the exception of Carti-Laps, which was measured in urine. The CartiLaps values were normalized by the creatinine results.

TABLE 2

Assays and Suppliers

| Biomarker | Assay type/format | Source |
|---|---|---|
| Anti-CCP | Sandwich ELISA, MTP | Axis-Shield, Dundee (UK) |
| CRP | Homogenous assay, Hitachi | Roche Diagnostics, Mannheim (FRG) |
| Hyaluronic acid | Sandwich ELISA, MTP | Chugai, Tokyo (J) |
| IL-6 | Sandwich ELISA, MTP | Roche Diagnostics, Mannheim (FRG) |
| RF | Homogenous assay, Hitachi | Roche Diagnostics, Mannheim (FRG) |
| SAA | Sandwich ELISA, MTP | Biosource, Nivelles (B) |
| pro-MMP-3 | Sandwich ELISA, MTP | The Binding Site, Birmingham (UK) |
| S100 A8/A9 | Sandwich ELISA, MTP | Bühlmann Lab., Allschwill (CH) |
| S100 A12 | Prototype ELISA, MTP | Roche Diagnostics, Penzberg (FRG) |
| Osteocalcin | Sandwich ELISA, Elecsys ® | Roche Diagnostics, Mannheim (FRG) |
| β-Crosslaps | Sandwich ELISA, Elecsys ® | Roche Diagnostics, Mannheim (FRG) |
| PINP | Sandwich ELISA, Elecsys ® | Roche Diagnostics, Mannheim (FRG) |
| sCD14 | Sandwich ELISA, MTP | IBL, Hamburg (FRG) |
| CartiLaps | Comp. ELISA, MTP | Nordic Bioscience, Herlev (DK) |
| ICTP | Comp. ELISA, MTP | Orion Diagnostika, Espoo (FIN) |
| sE-Selectin | Sandwich ELISA, MTP | R&D Systems, Minneapolis, (USA) |

EXAMPLE 5

Univariate Analysis

The baseline samples of all 237 RA patients were measured with the 16 markers listed in table 2. Each marker value was logarithmized and a ROC analysis was carried out. Table 3 represents the AUC values and the sensitivity (at a specificity of 90%) for each marker.

TABLE 3

Univariate analysis

| Biomarker | AUC (%) | Sensitivity (%) at a specificity of 90% |
|---|---|---|
| Anti-CCP | 59 | 5 |
| CRP | 75 | 37 |
| Hyaluronic acid | 70 | 20 |
| IL-6 | 77 | 32 |
| RF | 67 | 24 |
| SAA | 70 | 27 |
| pro-MMP-3 | 72 | 31 |
| S100 A8/A9 | 70 | 29 |
| S100 A12 | 68 | 32 |
| Osteocalcin | 50 | 8 |
| β-CrossLaps | 57 | 7 |
| PINP | 55 | 10 |
| sCD14 | 61 | 17 |
| CartiLaps | 71 | 19 |
| ICTP | 71 | 19 |
| sE-selectin | 67 | 20 |

8 markers achieved an AUC of 70% and higher. The best sensitivity showed CRP with 37% at a specificity of 90%. It was very surprising, that anti-CCP, which is published as a prognostic factor, showed only an AUC of 0.59. In many scientific papers biomarkers with an odds ratio of about 3.0 and higher are—rather optimistically referred to as predictors of progression. For example, Syversen, S. W., et. al. (Ann. Rheum. Dis. 65, Suppl. II (2006) 110) reported that anti-CCP (OR=4.18), RF-IgM (OR=3.12) ESR(OR=3.73) and female gender (OR=3.29) are independent predictors of 10-year radiographic progression in RA patients. If we calculate the Odds ratio of anti-CCP (Cut-off>5 U/mL) in our RA collective, we obtain a similar odds ratio, i.e. an OR of 4.6. Nevertheless an odds ratio of "4" or "5" has merely no diagnostic value in clinical routine, where a high specificity (corresponding to a low number of false positive results) is required.

EXAMPLE 6

Multi-Variate Analysis

Due to the limited number of RA patients with progression a randomly split of the patient collective into a training set and into a test set was not possible. Therefore an external cross validation (ECV) was carried out. For the ECV the training set was subdivided 50 times (ratio 2(training subsets):1(test subsets)) for an external Monte-Carlo cross validation (Dudoit, S. and van der Laan, M. J., Statistical Methodology 2 (2005) 131-154). On the training subsets a classification algorithm was develop and on the independent test subsets the algorithm was validated.

The classification algorithms were generated with the Regularized Discriminant Analysis (RDA), which is a generalization of the common Discriminant Analysis, i.e. Quadratic- and Linear Discriminant Analysis (McLachlan, G. J., Discriminant Analysis and Statistical Pattern Recognition, Wiley Series in probability and mathematical statistics, 1992). In the RDA alternatives to the usual maximum likelihood (plug-in) estimates for the covariance matrices are used. These alternatives are characterized by two parameters ($\lambda, \gamma$), the values of which are customized to individual situations by jointly minimizing a sample-based estimate of future misclassification risk (Friedman, J. H., J. of the American Statistical Association 84 (1989) 165-175). As an alternative method Support Vector Machines algorithms (Hastie, T., et al., The Elements of Statistical Learning, Springer Series in Statistics, 2001) can be fitted with comparable classification results.

The marker panels were stepwise constructed starting from the best single marker for the classification problem and ending when the total classification error do not change remarkable any more. In order to gain centralized distributions every single marker was transformed with the natural logarithmic function.

EXAMPLE 7

Identification of a Marker Panel for Assessing the Risk of Disease Progression of RA Patients The goal of the multivariate analysis was to find a marker panel, which shows a higher sensitivity than the best single marker. The specificity limit was set to 90%. The first marker selected was CRP with a sensitivity of 35% and the second one was IL-6 improving the sensitivity to 50%. There are some other combinations with different markers as the third and the fourth one, which are able to minimize the total error and/or to improve the sensitivity (Table 4). For all these marker combinations the most important two markers are CRP and IL-6, thereby representing the key markers of these marker panels.

The aim of the current invention is to aid the rheumatologist in his assessment whether an RA patient is at risk of disease progression. The diagnostic value of the identified marker panel is best reflected in Table 4 by the total error of the classification. CRP, currently a single biological marker used for the estimation of inflammation gives a total error of 0.228. IL-6 as a single marker also reveals a similar total error of 0.247. The preferred combination of CRP and IL 6 significantly improves the classification reducing the total error to 0.203. Adding a third and a fourth marker finally helps to further minimize the misclassification (total error 0.196). The achieved sensitivity of 50% suggests that based on the method disclosed here about one half of the RA-patients with a progressive disease can be identified correctly by biochemical markers measure at a single time point, i.e. at baseline, which is not possible so far. This classification is expected to aid the rheumatologist in the decision process for example to start a treatment using DMARDs or to change to a better therapy scheme using a combination of different DMARDs.

TABLE 4

Classification results of patients classified as RA with disease progression versus RA with no disease progression

| No of Markers | marker or marker panel | ECV (50 fold) | | |
|---|---|---|---|---|
| | | TOTAL ERROR | correct pos. Sensitivity | correct neg. Specificity |
| 1 | CRP | 0.228 | 35.0% | 91.5% |
| 1 | Il-6 | 0.247 | 35.0% | 88.1% |
| 2 | CRP, IL-6 | 0.203 | 50.0% | 91.5% |
| 3 | CRP, IL-6, S100 A8/A9 | 0.203 | 52.5% | 89.8% |
| 3 | CRP, IL-6, pro-MMP-3 | 0.203 | 55.0% | 89.8% |
| 4 | CRP, IL-6, S100 A8/A9, sE-Selectin | 0.196 | 55.0% | 89.8% |

The Boxplots for the markers CRP and IL-6 and marker combinations (CRP IL-6 and CRP+IL-6+pro-MMP3), respectively, of Table 4 are shown in FIGS. 2 to 5.

What is claimed is:
1. A method for aiding in assessing a risk of disease progression for a patient having rheumatoid arthritis (RA), the method comprising the steps of
  obtaining a liquid sample from the patient wherein the sample is selected from the group consisting of blood, serum, plasma, saliva, and synovial fluid,
  measuring in said sample a concentration value of C-reactive protein (CRP) and a concentration value of interleukin 6,
  mathematically combining the concentration values into a single combined value, and
  correlating the combined value to the risk of disease progression.
2. The method according to claim 1, wherein the patient is undergoing treatment with an anti-rheumatic drug selected from group consisting of disease modifying anti-rheumatoid drugs (DMARDs) when the assessment is performed.

* * * * *